United States Patent [19]

McKnight et al.

[11] Patent Number: 5,369,105

[45] Date of Patent: Nov. 29, 1994

[54] 7-((SUBSTITUTED)AMINO-8-((SUBSTITUTED)CARBONYL)-METHYLAMINO-1-OXASPIRO(4,5)DECANES USEFUL IN PARKINSON'S DISEASE, DYSTONIA, AND OTHER MOVEMENT DISORDERS

[75] Inventors: Alexander McKnight, Ely; Geoffrey N. Woodruff, Braughing Nr. Ware, both of United Kingdom

[73] Assignee: Warner-Lambert Company, Morris Plains, N.J.

[21] Appl. No.: 160,533

[22] Filed: Dec. 1, 1993

Related U.S. Application Data

[62] Division of Ser. No. 941,576, Sep. 8, 1992, Pat. No. 5,317,028.

[51] Int. Cl.$^5$ ............... A61K 31/335; A61K 31/38; A61K 31/445; A61K 31/55
[52] U.S. Cl. ...................... 514/212; 514/320; 514/323; 514/324; 514/409; 514/443; 514/462
[58] Field of Search ............... 514/212, 320, 323, 324, 514/409, 443, 462

[56] References Cited

U.S. PATENT DOCUMENTS

| | | | |
|---|---|---|---|
| 4,499,286 | 2/1985 | Binder | 548/527 |
| 4,598,087 | 7/1986 | Horwell | 514/429 |
| 4,663,343 | 5/1987 | Horwell et al. | 514/429 |
| 4,737,493 | 4/1988 | Horwell | 514/212 |
| 4,826,819 | 5/1989 | Vecchietti | 514/212 |
| 4,877,796 | 10/1989 | Clemence et al. | 514/311 |
| 4,950,760 | 8/1990 | Clemence et al. | 546/164 |
| 4,963,567 | 10/1990 | Clemence et al. | 514/314 |
| 4,965,278 | 10/1990 | Horwell et al. | 514/414 |
| 5,030,649 | 7/1991 | Vecchietti | 514/428 |
| 5,043,347 | 8/1991 | Clemence et al. | 514/409 |
| 5,063,242 | 11/1991 | Horwell et al. | 514/414 |
| 5,317,028 | 5/1994 | McKnight et al. | 514/409 |

FOREIGN PATENT DOCUMENTS

| | | |
|---|---|---|
| 0254545 | 1/1988 | European Pat. Off. |
| 0260555 | 3/1988 | European Pat. Off. |

OTHER PUBLICATIONS

*Movement Disorders*, vol. 6, No. 2, 1991 pp. 133–138. J. M. Brotchie, et al.

Lambert, P. D., et al., *Molecular Neuropharmacology* 1, 1991, 77–82.

Singh, L., et al., *European J. of Pharm*, 191, 1990, 477–480.

Richter, A., et al., *Neuroscience Letters*, 133,1: 1991, 57–60.

Schmidt, W. J., et al., *Trends in Neuroscience*, 13,2: 1990, 46–47.

*Primary Examiner*—Richard L. Raymond
*Attorney, Agent, or Firm*—Elizabeth M. Anderson

[57] ABSTRACT

Methods for using substituted phenoxy-, 1-, and 2-naphthalenyloxy-, indenyl-, indolyl-, benzo[b]furanyl-, and benzo[b]thienylcarboxamides of 7,8-(substituted-diamino)-1-oxaspiro[4.5]decanes as agents for alleviating the symptoms of Parkinson's disease, dystonia, and other movement disorders are disclosed. Pharmaceutical compositions employing the compounds are also disclosed.

4 Claims, 4 Drawing Sheets

7-((SUBSTITUTED)AMINO-8-((SUBSTITUTED)-CARBONYL)-METHYLAMINO-1-OXASPIRO(4,5)-DECANES USEFUL IN PARKINSON'S DISEASE, DYSTONIA, AND OTHER MOVEMENT DISORDERS

This is a divisional application of U.S. Ser. No. 07/941,576 filed Sep. 8, 1992, now U.S. Pat. No. 5,317,028.

BACKGROUND OF THE INVENTION

The present invention is related to a method of using 7-((substituted) amino-8-((substituted) carbonyl)-methylamino)-1-oxaspiro(4.5)decanes and the pharmaceutically acceptable salts thereof as agents useful in treating Parkinson's disease, dystonia, and other movement disorders. The compounds, processes for preparing them, and pharmaceutical compositions containing them are found in U.S. Pat. No. 4,737,493, which is herein incorporated by reference. The disclosed utility in the patent is analgesic. The compounds are also disclosed as having sedative, diuretic, and corticosteroid elevating effects and therefore as being useful diuretic and psychotherapeutic agents.

U.S. Pat. No. 4,965,278 and its divisional U.S. Pat. No. 5,063,242 cover use of the above compounds for inflammation, stroke, and cerebrovascular disorders such as cerebral ischemia and infarction. These two patents are hereby incorporated by reference.

U.S. Pat. No. 4,598,087 covers certain substituted trans-1,2-diamino-cyclohexyl amide compounds which demonstrate selective opioid receptor binding. They are disclosed as useful as analgesics, diuretics, and psychotherapeutic agents.

U.S. Pat. No. 4,663,343 covers certain substituted naphthalenyloxy-1,2-diaminocyclohexyl amide compounds which possess selective kappa opioid receptor site binding activity and are useful as analgesics and diuretics.

European Application 258,095A discloses decahydroquinoline derivatives and European application 258,096 covers 1,2-diaminoindane derivatives. The compounds are analgesics with strong affinity for opiate receptors. The compounds are also mentioned as having diuretic, antiarrhythmic, cerebral antiischemic and hypotensive activity.

European Application 260,041 covers 1-acylsubstituted piperidine derivatives useful as analgesics with specific agonist effect on Kappa opioid receptors.

European Application 261,842 covers certain acylated-(1-(phenyl or benzyl)-1,2-ethylene diamines which are K-receptor agonists which act as analgesics through interaction with kappa opioid receptors.

European Application 254,545 covers 1,2-ethylene diamine compounds having analgesic, diuretic and antiinflammatory activity.

U.S. Pat. No. 4,499,286 covers transcyclohexane-1,2-diamine derivatives of thienylacetic acid. The compounds are disclosed as having analgesic activity.

European Application 260,555 covers benzo-fused cycloalkane and oxa- and thia-, cycloalkane trans-1,2-diamine derivatives useful as analgesic and diuretics.

SUMMARY

The present invention relates to a novel therapeutic means for alleviating Parkinsonian symptoms, dystonia, and other movement disorders. The method of treatment comprises administering to a patient in need of such treatment a therapeutically effective amount of a compound of Formula I as described hereinafter.

Pharmaceutical compositions are also included in the present invention.

BRIEF DESCRIPTION OF THE DRAWINGS

FIGS. IA and B

In FIGS. IA and B the effect of Compound I on excitatory amino acid release in the substantia nigra reticulata is shown. The time in minutes is versus the [$^3$H]glutamate release.

Slices of SNR loaded with [$^3$H]glutamate. Release of this loaded glutamate was monitored using standard superperfusion techniques. At time 45 to 50 minutes test compounds were added.

a) 40 mM K$^+$ causes Ca$^{2+}$-dependent release of glutamate.

b) In the presence of 1 μM Compound I the release induced by 40 mM K$^+$ was completely inhibited.

(Data are means ±SEM, N=6)

FIG. II

FIG. II shows the anti-Parkinsonian effect of Compound I injections in the rat entopeduncular nucleus. The amount of Compound I is versus the locomotor score.

Rats were rendered Parkinsonian by injection of reserpine (4 mg/kg). This treatment resulted in akinesia and rigidity. Locomotor scores were measured following injections directly into the entopeduncular nucleus unilaterally. Locomotor scores relate to distance moved by the animals. Following injection of vehicle, the animals remained Parkinsonian and attained very low locomotor scores. With increasing doses of Compound I, increasing amounts of locomotor activity were sen. These anti-Parkinsonian effects were also accompanied by reductions in rigidity.

FIG. III

In FIG. III the anti-Parkinsonian effect of Compound I injections in the medial globus pallidus (GPM) in the primate rendered Parkinsonian is shown. The amounts of Compound I are versus the mobility score.

Mobility scores are shown for marmosets pre- and posttreatment with MPTP (N=4). Mobility scores are derived from a clinical rating scale. Mobility was measured in an MPTP-treated Parkinsonian marmoset following bilateral injections of Compound I into the GPM. Following injections of 20 mM and 50 mM Compound I a marked reversal of Parkinsonian rigidity and akinesia was seen. The animals' locomotor activity returned to near normal levels. At the higher dose, the latency of onset was very short (less than 4 minutes) but some stereotyped movements were seen. At the lower dose of Compound I, the anti-Parkinsonian effects had a longer latency of onset (approximately 25 minutes) but no stereotypy was seen. Further studies are, however, needed to clarify whether these anti-Parkinsonian effects represent a return to normal mobility. The anti-Parkinsonian effects of Compound I were totally inhibited by naloxone (5 mg/kg).

DETAILED DESCRIPTION

The present invention provides certain substituted oxaspirodiaminocyclohexane compounds which are useful as agents for alleviating Parkinsonian symptoms, dystonia, and other movement disorders. The compounds are

I wherein
n is an integer of from one to six;
either of X or Y is oxygen and the other is —CH$_2$—;
R$_1$ is selected from
a)

where R$_4$ and R$_5$ are independently hydrogen, fluorine, chlorine, bromine, nitro, trifluoromethyl, alkyl of from one to six carbon atoms, alkoxy of from one to six carbon atoms, or aryl;

b) 3,4,5-trimethylphenoxy;

c)

where R$_6$ is hydrogen, fluorine, chlorine, alkyl of from one to six carbon atoms, or aryl; Z is —CH$_2$—, —O—, —S—, or —NR$_7$— where R$_7$ is hydrogen, alkanoyl of from one to six carbon atoms, or alkyl of from one to six carbon atoms;

d)

where R$_8$ and R$_9$ are independently hydrogen, fluorine, bromine, alkyl of from one to six carbon atoms, or alkoxy of from one to four carbon atoms; or e)

where R$_8$ and R$_9$ are as defined above; R$_2$ is methyl and R$_3$ is hydrogen, alkyl of from one to six carbon atoms, where R$_{10}$ is alkyl of from one to four carbon atoms; or where R$_2$ and R$_3$ when taken together with the nitrogen atom to which they are attached, form a pyrrolidinyl, piperidinyl, or hexahydro-1H-azepinyl ring; and the pharmaceutically acceptable acid addition salts thereof.

The compounds of the present invention constitute a class of derivatives of certain substituted oxaspirodiaminocyclohexane compounds of Formula I above in which one nitrogen atom is an amine nitrogen substituted with methyl and a second substituent selected from the group R$_3$ as defined above, or when taken together with the nitrogen atom to which they are attached, R$_2$ and R$_3$ form a pyrrolidinyl, piperidinyl, or hexahydro-1H-azepinyl ring, and the other nitrogen atom is a N-methyl amide nitrogen further substituted with the group R$_1$ as defined above.

Compounds of the present invention contain one or more asymmetric carbon atoms and therefore exist in various stereoisomeric forms. Additionally, the compounds of this invention are capable of existing in different geometric isomeric forms. For example, the oxygen atom of the 5-membered spiro-ring may be positioned on the same side of the average plane of the cyclohexane ring as the amide nitrogen, or on the side opposite. The present invention contemplates all geometric and stereoisomeric forms of the compounds of Formula I above.

The individual stereoisomers are obtained, if desired, from mixture of the different forms by known methods of resolution such as the formation of diastereomers, followed by recrystallization.

Compounds of the instant invention include solvates, hydrates, and salts of Formula I above.

Preferred compounds of the present invention are those of Formula I above wherein R$_1$ is where R₄ and R₅ are independently hydrogen, fluorine, chlorine, bromine, nitro, trifluoromethyl, alkyl of from one to six carbon atoms, alkoxy of from one to six carbon atoms, or aryl.

By the term "aryl" is meant phenyl; phenyl substituted with fluorine, chlorine, alkoxy of from one to four carbon atoms, nitro, or trifluoromethyl; 2- or 3-thienyl; and 2- or 3-thienyl substituted with alkyl of from one to four carbon atoms or alkoxy of from one to four carbon atoms.

Preferred compounds of the present invention are those of Formula I above where R₁ is wherein R₆ is as defined above. The most preferred compounds are substituted inden-1-yl compounds of Formula I above.

Other preferred compounds of the present invention are those of Formula I wherein R₁ is wherein R₆ is as defined above. The most preferred compounds are substituted benzofuran-4-yl compounds of Formula I.

Yet other preferred compounds of the present invention are those of Formula I wherein R₁ is wherein R₆ is as defined above. The most preferred compounds are substituted benzo[b]thiophen-4-yl compounds of Formula I.

Yet other preferred compounds of the present invention are those of Formula I wherein R₁ is wherein R₆ and R₇ are as defined above. The most preferred compounds are indol-4-yl compounds of Formula I.

Yet other preferred compounds of the present invention are those of Formula I wherein R₁ is wherein R₈ and R₉ are independently hydrogen, fluorine, chlorine, bromine, alkyl of from one to four carbon atoms or alkoxy of from one to four carbon atoms.

Preferred substituents for R₂ and R₃ are those where R₂ is methyl and R₃ is lower alkyl, most preferably methyl, or where R₂ and R₃ taken together with the nitrogen atom to which they are attached form a pyrrolidinyl ring.

Preferred compounds of the present invention include but are not limited to:

[5R-(5α,7α,8β)]-N-Methyl-N-[7-(methyl-2-propynyl-amino)-1-oxaspiro[4.5]dec-8-yl]-2-phenoxyacetamide,

[5S-(5α,7α,8β)]-N-Methyl-N-[7-(methyl-2-propynyl-amino)-1-oxaspiro[4.5]dec-8-yl]-2-phenoxyacetamide,

[5R-(5α,7β,8α)]-N-Methyl-N-[7-(methyl-2-propynyl-amino)-1-oxaspiro[4.5]dec-8-yl]-2-phenoxyacetamide,

[5S-(5α,7β,8α)]-N-Methyl-N-[7-(methyl-2 -propynyl-amino)-1-oxaspiro[4.5]dec-8-yl]-2-phenoxyacetamide,

[5R-(5α,7α,8β)]-2-(4-Fluorophenoxy)-N-methyl-N-[7-(1-pyrrolidinyl)]-1-oxaspiro[4.5]dec-8-yl]acetamide,

[5S-(5α,7α,8β)]-2-(4-Fluorophenoxy)-N-methyl-N-[7-(1-pyrrolidinyl)]-1-oxaspiro[4.5]dec-8-yl]acetamide,

[5R-(5α,7β,8α)]-2-(4-Fluorophenoxy)-N-methyl-N-[7-(1-pyrrolidinyl)]-1-oxaspiro[4.5]dec-8-yl]acetamide,

[5S-(5α,7β,8α)]-2-(4-Fluorophenoxy)-N-methyl-N-[7-(1-pyrrolidinyl)]-1-oxaspiro[4.5]dec-8-yl]acetamide,

[5R-(5α,7α,8β)]-2-(4-Fluorophenoxy)-N-methyl-N-[7-[methyl-(2-phenylethyl)amino]-1-oxaspiro[4.5]dec-[5R-(5α,7α,8β)]-2-(4-Fluorophenoxy)-N-methyl-N-8-yl]acetamide,

[5S-(5α,7α,8β)]-2-(4-Fluorophenoxy)-N-methyl-N-[7-[methyl-(2 -phenylethyl)amino]-1-oxaspiro[4.5]dec-8-yl]acetamide,

[5R-(5α,7β,8α)]-2-(4-Fluorophenoxy)-N-methyl-N-[7-[methyl-(2-phenylethyl)amino]-1-oxaspiro[4.5]dec-8-yl]acetamide,

[5S-(5α,7β,8α)]-2-(4-Fluorophenoxy)-N-methyl-N-[7-[methyl-(2-phenylethyl)amino]-1-oxaspiro[4.5]dec-8-yl]acetamide,

[5R-(5α,7α,8β)]-N-Methyl-2-(3-nitrophenoxy )-N-[7-(1-pyrrolidinyl)-1-oxaspiro[4.5]dec-8-yl]acetamide,

[5S-(5α,7α,8β)]-N-Methyl-2-(3-nitrophenoxy )-N-[7-(1-pyrrolidinyl)-1-oxaspiro[4.5]dec-8-yl]acetamide,

[5R-(5α,7β,8α)]-N-Methyl-2-(3-nitrophenoxy)-N-[7-(1-pyrrolidinyl )-1-oxaspiro[4.5]dec-8-yl]acetamide,

[5S-(5α,7β,8α)]-N-Methyl-2-(3-nitrophenoxy)-N-[7-(1-pyrrolidinyl)-1-oxaspiro[4.5]dec-8-yl]acetamide,

[5R-(5α,7α,8β)]-N-Methyl-N-[7-(1-pyrrolidinyl)-1-oxaspiro[4.5]dec-8-yl]-2-[3-(trifluoromethyl)phenoxy]acetamide,

[5S-(5α,7α,8β)]-N-Methyl-N-[7-(1-pyrrolidinyl)-1-oxaspiro[4.5]dec-8-yl]-2-[3-(trifluoromethyl)phenoxy]acetamide,

[5R-(5α,7β,8α)]-N-Methyl-N-[7-(1-pyrrolidinyl)-1-oxaspiro[4.5]dec-8-yl]-2 -[3-(trifluoromethyl)phenoxy]acetamide,

[5S-(5α,7β,8α)]-N-Methyl-N-[7 -(1-pyrrolidinyl)-1-oxaspiro[4.5]dec-8-yl]-2-[3-(trifluoromethyl)phenoxy]acetamide,

[5R-(5α,7α,8β)]-2-(3,4-Dichlorophenoxy)-N-methyl-N-[7-(1-pyrrolidinyl)-1-oxaspiro[4.5]dec-8-yl]-acetamide,

[5S-(5α,7α,8β)]-2-(3,4-Dichlorophenoxy)-N-methyl-N-[7-(1-pyrrolidinyl)-1-oxaspiro[4.5]dec-8-yl]-acetamide,

[5R-(5α,7β,8α)]-2-(3,4-Dichlorophenoxy)-N-methyl-N-[7-(1-pyrrolidinyl)-1-oxaspiro[4.5]dec-8-yl]-acetamide,

[5S-(5α,7β,8α)]-2-(3,4-Dichlorophenoxy)-N-methyl-N-[7-(1-pyrrolidinyl)-1-oxaspiro[4.5]dec-1]-acetamide,

[5R-(5α,7α,8β)]-2-(2,6-Dichlorophenoxy)-N-methyl-N-[7-(1-pyrrolidinyl)-1-oxaspiro[4.5]dec-8-yl]-acetamide,

[5S-(5α,7α,8β)]-2-(2,6-Dichlorophenoxy)-N-methyl-N-[7-(1-pyrrolidinyl)-1-oxaspiro[4.5]dec-8-yl]-acetamide,

[5R-(5α,7β,8α)]-2-(2,6-Dichlorophenoxy)-N-methyl-N-[7-(1-pyrrolidinyl)-1-oxaspiro[4.5]dec-8-yl]-acetamide,

[5S-(5α,7β,8α)]-2-(2,6-Dichlorophenoxy)-N-methyl-N-[7-(1-pyrrolidinyl)-1-oxaspiro[4.5]dec-8-yl]-acetamide,

[5R-(5α,7α,8β)]-2-(3,5-Dichlorophenoxy)-N-methyl-N-[7-(1-pyrrolidinyl)-1-oxaspiro[4.5]dec-8-yl]-acetamide,

[5S-(5α,7α,8β)]-2-(3,5-Dichlorophenoxy)-N-methyl-N-[7 -(1-pyrrolidinyl)-1-oxaspiro[4.5]dec-8-yl]-acetamide,

[5R-(5α,7β,8α)]-2-(3,5-Dichlorophenoxy)-N-methyl-N-[7-(1-pyrrolidinyl)-1-oxaspiro[4.5]dec-8-yl]-acetamide,

[5S-(5α,7β,8α)]-2-(3,5-Dichlorophenoxy)-N-methyl-N-[7 -(1-pyrrolidinyl)-1-oxaspiro[4.5]dec-8-yl]-acetamide,

[5R-(5α,7α,8β )]-N-Methyl-2-(1-naphthalenyloxy)-N-[7-(1-pyrrolidinyl)-1-oxaspiro[4.5]dec-8-yl]acetamide,

[5S-(5α,7α,8β)]-N-Methyl-2-(1-naphthalenyloxy)-N-[7-(1-pyrrolidinyl)-1-oxaspiro[4.5]dec-8-yl]acetamide,

[5R-(5α,7β,8α)]-N-Methyl-2-(1-naphthalenyloxy)-N-[7-(1-pyrrolidinyl)-1-oxaspiro[4.5]dec-8-yl]acetamide,

[5S-(5α,7β,8α)]-N-Methyl-2-(1-naphthalenyloxy)-N-[7-(1-pyrrolidinyl)-1-oxaspiro[4.5]dec-8-yl]acetamide,

[5R-(5α,7α,8β)]-N-Methyl-2-(2-naphthalenyloxy)-N-[7-(1-pyrrolidinyl)-1-oxaspiro[4.5]dec-8-yl]acetamide,

[5S-(5α,7α,8β)]-N-Methyl-2-(2-naphthalenyloxy)-N-[7-(1-pyrrolidinyl)-1-oxaspiro[4.5]dec-8-yl]acetamide,

[5R-(5α,7β,8α)]-N-Methyl-2-(2-naphthalenyloxy)-N-[7-(1-pyrrolidinyl)-1-oxaspiro[4.5]dec-8-yl]acetamide,

[5S-(5α,7β,8α)]-N-Methyl-2-(2-naphthalenyloxy)-N-[7-(1-pyrrolidinyl)-1-oxaspiro[4.5]dec-8-yl]acetamide,

[5R-(5α,7α,8β)]-N-Methyl-N-[7-[methyl[2-(2-thienyl)ethyl]amino]-1-oxaspiro[4.5]dec-8-yl]-2-(1-naphthalenyloxy)acetamide,

[5S-(5α,7α,8β)]-N-Methyl-N-[7-[methyl[2-(2-thienyl)ethyl]amino]-1-oxaspiro[4.5]dec-8-yl]-2-(1-naphthalenyloxy)acetamide,

[5R-(5α,7β,8α)]-N-Methyl-N-[7-[methyl[2-(2-thienyl)ethyl]amino]-1-oxaspiro[4.5]dec-8-yl]-2-(1-naphthalenyloxy)acetamide,

[5S-(5α,7β,8α)]-N-Methyl-N-[7-[methyl[2-(2-thienyl)ethyl]amino]-1-oxaspiro[4.5]dec-8-yl]-2-(1-naphthalenyloxy)acetamide,

[5R-(5α,7α,8β)]-N-Methyl-N-[7-(methyl-2-propenyl-amino)-1-oxaspiro[4.5]dec-8-yl]-1H-indene-3-acetamide,

[5S-(5α,7α,8β)]-N-Methyl-N-[7-(methyl-2-propenyl-amino)-1-oxaspiro[4.5]dec-8-yl]-1H-indene-3-acetamide,

[5R-(5α,7β,8α)]-N-Methyl-N-[7-(methyl-2-propenyl-amino)-1-oxaspiro[4.5]dec-8-yl]-1H-indene-3-acetamide,

[5S-(5α,7β,8α)]-N-Methyl-N-[7-(methyl-2-propenyl-amino)-1-oxaspiro[4.5]dec-8-yl]-1H-indene-3-acetamide,

[5R-(5α,7α,8β)]-N-Methyl-[7-(1-pyrrolidinyl)-1-oxaspiro[4.5]dec-8-yl]-1H-indene-3-acetamide,

[5S-(5α,7α,8β)]-N-Methyl-[7-(1-pyrrolidinyl)-1-oxaspiro[4.5]dec-8-yl]-1H-indene-3-acetamide,

[5R-(5α,7β,8α)]-N-Methyl-[7-(1-pyrrolidinyl)-1-oxaspiro[4.5]dec-8-yl]-1H-indene-3-acetamide,

[5S-(5α,7β,8α)]-N-Methyl-[7-(1-pyrrolidinyl)-1-oxaspiro[4.5]dec-8-yl]-1H-indene-3-acetamide,

[5R-(5α,7α,8β)]-N-[7-(Dimethylamino )-1-oxaspiro[4.5]dec-8-yl]-N-methyl-1H-indole-3-acetamide,

[5S-(5α,7α,8β)]-N-[7-(Dimethylamino)-1-oxaspiro[4.5]dec-8-yl]-N-methyl-1H-indole-3-acetamide,

[5R-(5α,7β,8α)]-N-[7-(Dimethylamino)-1-oxaspiro[4.5]dec-8-yl]-N-methyl-1H-indole-3-acetamide,

[5S-(5α,7β,8α)]-N-[7-(Dimethylamino)-1-oxaspiro[4.5]dec-8-yl]-N-methyl-1H-indole-3-acetamide,

[5R-(5α,7α,8β)]-N-Methyl-N-[7-(1-pyrrolidinyl)-1-oxaspiro[4.5]dec-8-yl]-1H-indole-3-acetamide,

[5S-(5α,7α,8β)]-N-Methyl-N-[7-(1-pyrrolidinyl)-1-oxaspiro[4.5]dec-8-yl]-1H-indole-3-acetamide,

[5R-(5α,7β,8α)]-N-Methyl-N-[7-(1-pyrrolidinyl)-1-oxaspiro[4.5]dec-8-yl]-1H-indole-3-acetamide, [5S-(5α,7β,8α)]-N-Methyl-N-[7-(1-pyrrolidinyl)-1-oxaspiro[4.5]dec-8-yl]-1H-indole-3-acetamide,

[5R-(5α,7α,8β)]-N-Methyl-N-[7-(1-pyrrolidinyl)-1-oxaspiro[4.5]dec-8-yl]-2-benzofuranacetamide,

[5S-(5α,7α,8β)]-N-Methyl-N-[7-(1-pyrrolidinyl)-1-oxaspiro[4.5]dec-8-yl]-2 -benzofuranacetamide,

[5R-(5α,7β,8α)]-N-Methyl-N-[7-(1-pyrrolidinyl)-1-oxaspiro[4.5]dec-8-yl]-2-benzofuranacetamide,

[5S-(5α,7β,8α)]-N-Methyl-N-[7-(1-pyrrolidinyl)-1-oxaspiro[4.5]dec-8-yl]-2-benzofuranacetamide,

[5R-(5α,7α,8β)]-N-Methyl-N-[7-(1-pyrrolidinyl)-1-oxaspiro[4.5]dec-8-yl]-3-benzofuranacetamide,

[5S-(5α,7α,8β)]-N-Methyl-N-[7-(1-pyrrolidinyl)-1-oxaspiro[4.5]dec-8-yl]-3-benzofuranacetamide,

[5R-(5α,7β,8α)]-N-Methyl-N-[7-(1-pyrrolidinyl)-1-oxaspiro[4.5]dec-8-yl]-3-benzofuranacetamide,

[5S-(5α,7β,8α)]-N-Methyl-N-[7-(1-pyrrolidinyl)-1-oxaspiro[4.5]dec-8-yl]-3-benzofuranacetamide,

[5R-(5α,7α,8β)]-N-Methyl-N-[7-(1-pyrrolidinyl)-1-oxaspiro[4.5]dec-8-yl]-4-benzofuranacetamide,

[5S-(5α,7α,8β)]-N-Methyl-N-[7-(1-pyrrolidinyl)-1-oxaspiro[4.5]dec-8-yl]-4-benzofuranacetamide,

[5S-(5α,7β,8α)]-N-Methyl-N-[7-(1-pyrrolidinyl)-1-oxaspiro[4.5]dec-8-yl]-4-benzofuranacetamide,

[5R-(5α,7α,8β)]-N-[7-[(Cyclopropylmethyl)methylamino]-1-oxaspiro[4.5]dec-8-yl]-N,2-dimethyl-3-benzofuranacetamide,

[5S-(5α,7α,8β)]-N-[7-[(Cyclopropylmethyl)methylamino]-1-oxaspiro[4.5]dec-8-yl]-N,2-dimethyl-3-benzofuranacetamide,

[5R-(5α,7β,8α)]-N-[7-[(Cyclopropylmethyl)methylamino]-1-oxaspiro[4.5]dec-8-yl]-N,2 -dimethyl-3-benzofuranacetamide,

[5S-(5α,7β,8α)]-N-[7-[(Cyclopropylmethyl)methylamino]-1-oxaspiro[4.5]dec-8-yl]-N,2-dimethyl-3-benzofuranacetamide.

More preferred compounds of the present invention include but are not limited to:

(−) (5α,7α,8β)-N-methyl-N-[7-pyrrolidinyl)-1-oxaspiro[4.5]dec-8-yl]-4-benzo[b]furacetamide (Compound I), and (−)-(5α,7α,8β)-N-7-(1-pyrrolidinyl)-1-oxaspiro[4.5]-dec-8-yl]-4-benzo[b]thiophene-4-acetamide The compounds of Formula I of the present invention have a very high kappa opioid affinity, selectivity and potency. For example, (−)-(5α-7α-8β)-N-methyl-N-[7-(1-pyrrolidinyl)-1-oxaspiro[4.5]dec-8-yl]-4-benzo[b]furanacetamide gives a Ki of 0.73 nM with a μ/kappa ratio of 798. The $MPE_{50}$ in the rat paw pressure test for analgesia is 0.030 (iv).

This is considerably better than any selective kappa opioid compound known to the inventors.

The effectiveness of the aforementioned compounds as agents for Parkinson's disease, dystonia, and other movement disorders is determined by a pharmacological test procedure as described and illustrated below.

Current therapies for Parkinson's disease rely on dopamine agonist therapies to replace dopamine depletion in the striatum. However, these treatments are often plagued by debilitating side effects. Recent insights into the neural mechanisms underlying Parkinsonism may point the way to novel nondopaminergic therapies for Parkinsonism.

The neural mechanisms underlying Parkinsonism are characterized by overactivity of an excitatory amino acid (EAA), such as glutamate, utilizing input from the subthalamic nucleus to both the medial segment of the globus pallidus (GPM) and substantia nigra pars reticulata (SNR). Reduction of this overactivity by lesion of the subthalamic nucleus alleviates Parkinsonian symptoms in the primate. Similarly, blockade of EAA receptors locally in the GPM or SNR can also alleviate Parkinsonism.

The ubiquity of EAA transmission throughout the central nervous system (CNS) necessitates the reduction of EAA transmission in the GPM and SNR selectively if one is to develop a novel pharmaceutical that can alleviate Parkinsonism without compromising other EAA-related functions, e.g., learning and memory. One way in which this is achieved is to use compounds that interact with the peptide systems that modulate EAA transmission. In some regions of the CNS kappa opioid agonists can reduce FAA release. The major endogenous agonist for the kappa receptor is thought to be dynorphin. The distribution of dynorphin within the brain is interesting in that it is found in remarkably high levels within those areas receiving overactive EAA input in Parkinsonism, i.e., the GPM and SNR. In these areas dynorphin is thought to be a co-transmitter in the striatopallidal and striatonigral pathways. Kappa opioids might therefore provide an anatomically selective means by which to manipulate EAA transmission in the GPM and SNR.

Three experiments have provided answers important to relating the compounds of the invention to Compound I and Parkinsonism.

In Vitro EAA Release Studies in the Substantia Nigra

Figure 1A:
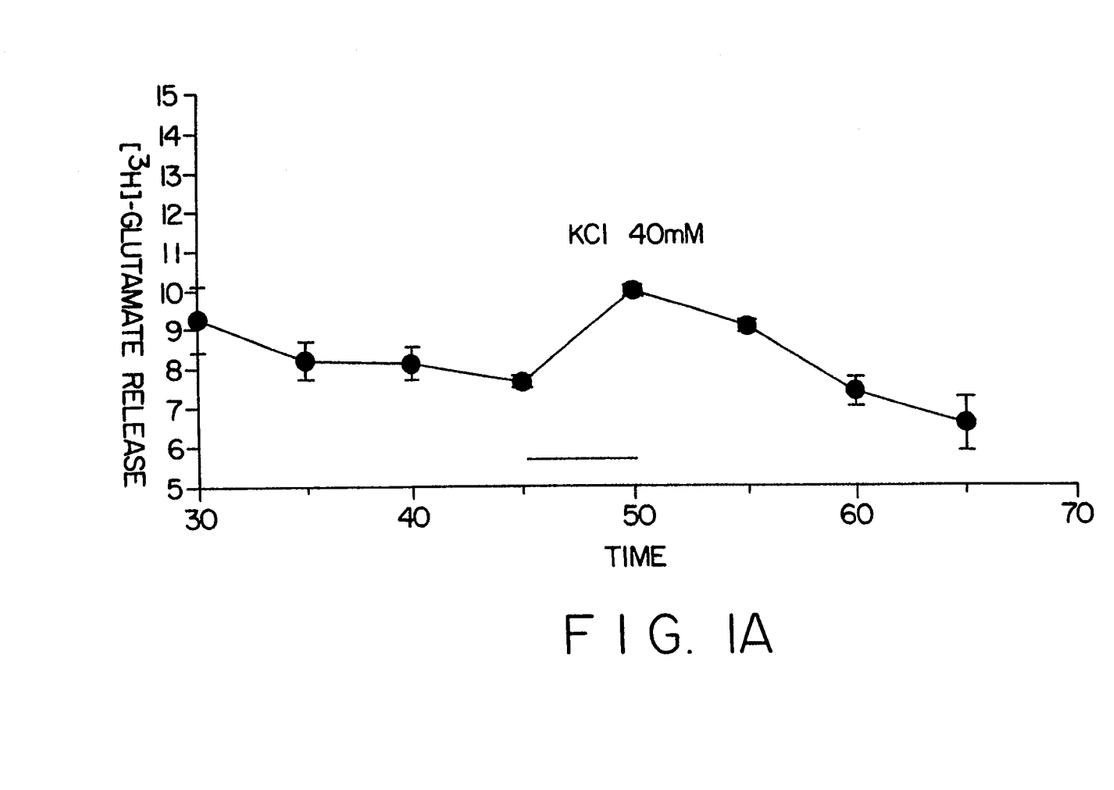
Figure 1B:
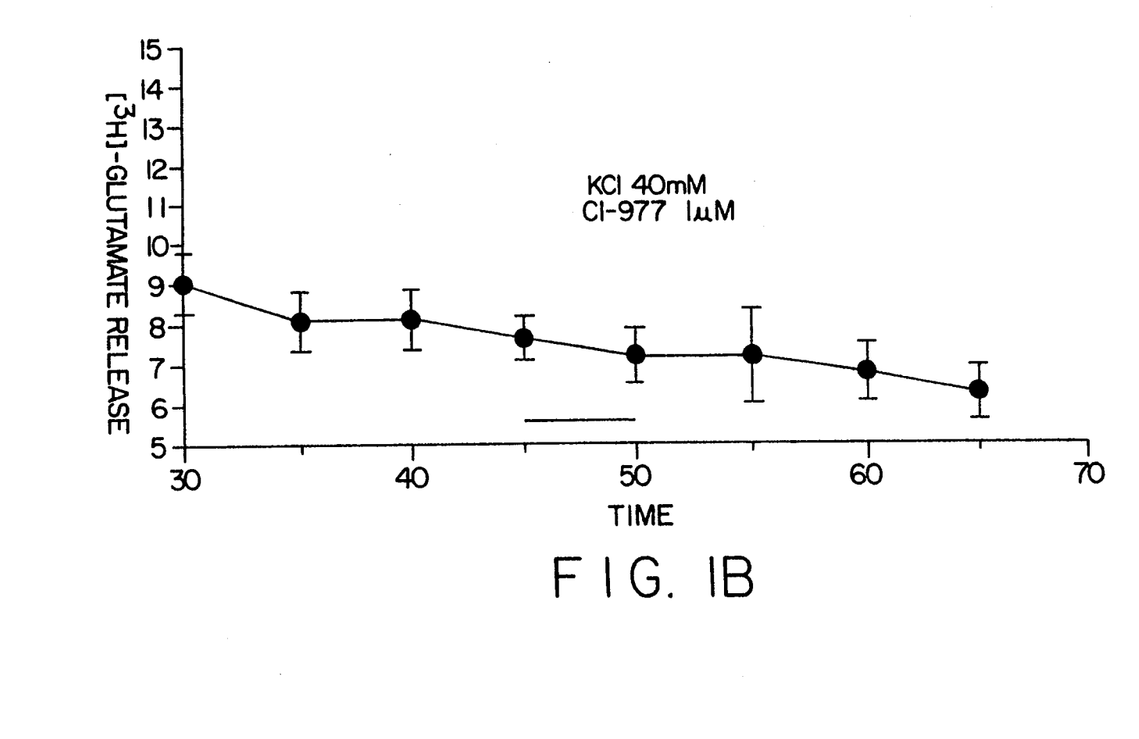

In slices of SNR from rat we have shown that $K^+$-evoked, $Ca^{2+}$-dependent release of preloaded [³H]glutamate is attenuated by over 98% in the presence of 1 μM Compound I (FIG. 1). Similar results are seen with 10 nM dynorphin.

Intracerebral Injections of Compound I in Parkinsonian Rats

Figure 2:
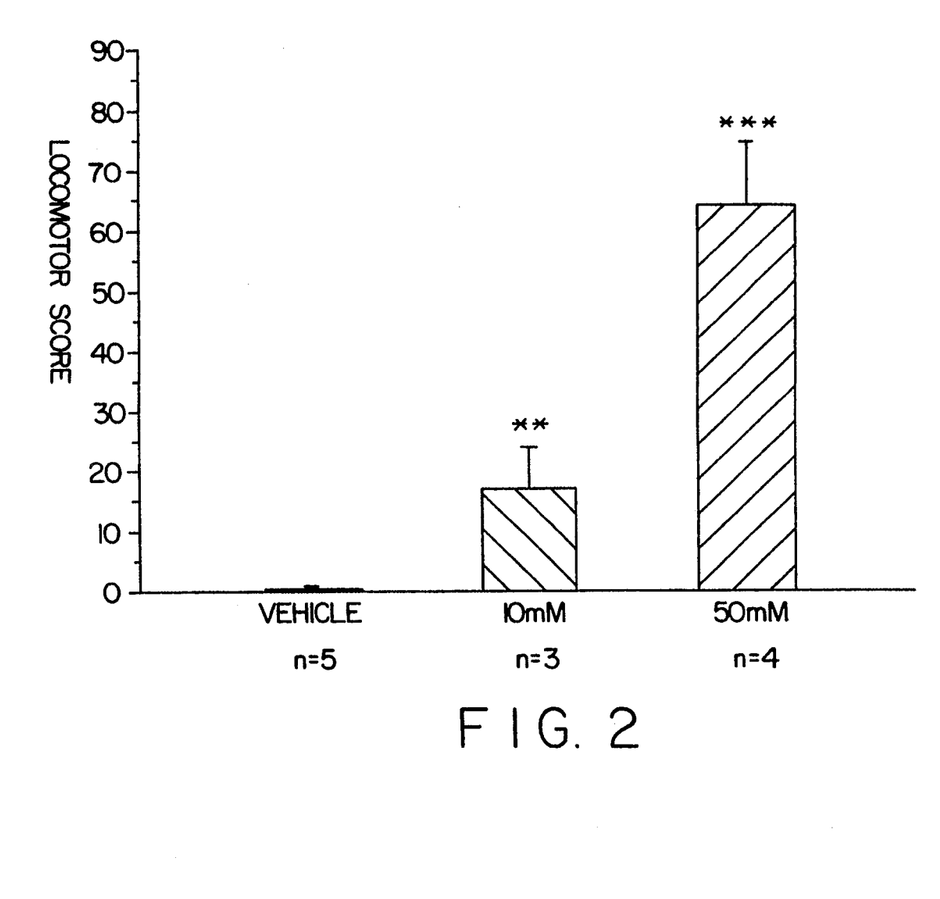

In the reserpine-treated Parkinsonian rat, unilateral injections of Compound I directly into the entopeduncular nucleus (rodent homologue of the GPM) provide a marked dose-dependent alleviation of Parkinsonian symptoms (FIG. 2).

Intracerebral Injections of Compound I in the MPTP-Treated Primate

Figure 3:
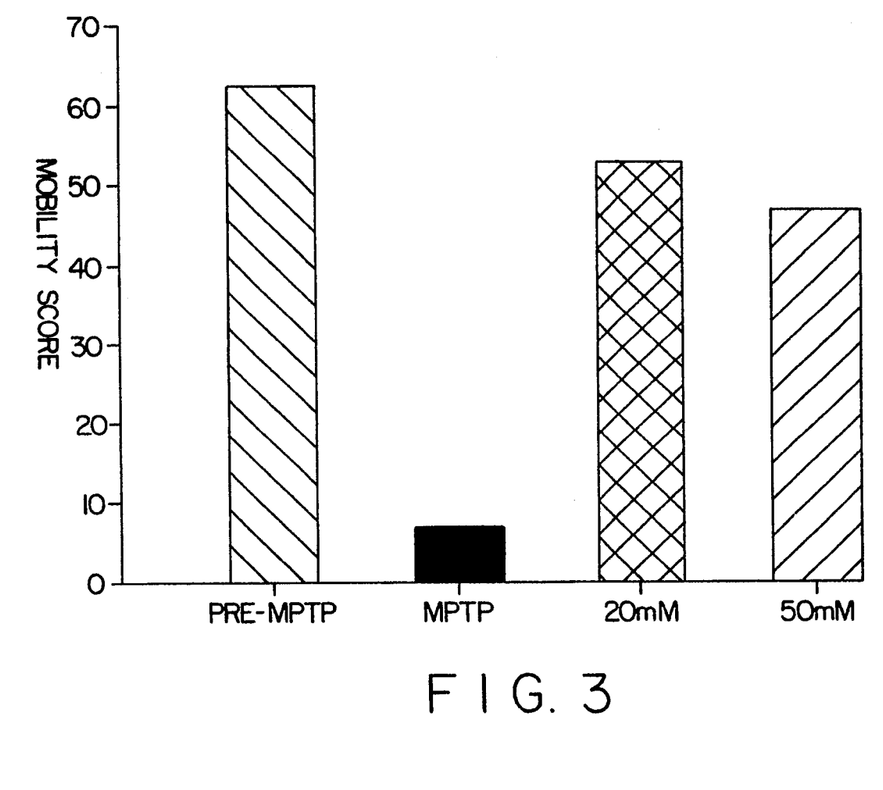

In the MPTP-primate, preliminary results would also suggest that Compound I has powerful anti-Parkinsonian effects (FIG. 3). Following injections of Compound I the mobility scores of MPTP-treated marmosets returned to near normal levels.

Methodology of EAA Release Studies

Detailed methodologies for the techniques used for the intracerebral injections and MPTP administration are given in (Brotchic JM, et al, *Movement Disorders* 1991;6(2):133–8).

Slices (400 μm) of substantia nigra were cut on a McIlwain tissue chopper. Slices were preloaded with [³H]L-glutamate (100 nM) for 30 minutes in Ringer's solution [containing amino-oxyacetic acid (50 μM), 30° C., pH 7.4, aerated with 95% $O_2$/5% $CO_2$]. $Ca^{2+}$-dependent, $K^+$-evoked release of glutamate from nigral slices was assayed using a release manifold similar in design to that used to measure release of preloaded radioactivity from rat portal vein (Hamilton T C, Weir S W, Weston A H, *Br J Pharmacol* 1986;88:103–11). This apparatus permitted the support and constant aeration of six slices at a time. Slices supported in the manifold were immersed in 4 mL of Ringer's containing 100 μM dihydrokainate to prevent reuptake of glutamate. After 5 minutes the slices were moved into a further vial containing 4 mL of Ringer's. The amount of radioactivity released from the slice in each 5-minute period was measured by liquid scintillation counting of an aliquot taken from each 4 mL of Ringer's. Release per 5 minutes was measured in this way for a total of 70 minutes. At the end of the experiment the nigral slice was placed in Triton X-100 for 24 hours to release all remaining radioactivity from the tissue. The amount of radioactivity in the slice was then determined. EAA release was expressed as a fractional release rate (percentage of that present at the start of each time interval). At time 45 minutes the slice was immersed in Ringer's modified to contain 40 mM $K^+$. This potassium pulse was used to evoke release of glutamate from the slice. The calcium-dependence of the release was demonstrated by replacing the $CaCl_2$ in the Ringer's solution by $CoCl_2$. The effects of Compound I on $K^+$-evoked release were demonstrated by adding Compound I (1 μM) to the potassium pulse solution.

From these studies we conclude that Compound I and other kappa opioids are able to modulate EAA release in the output regions of the basal ganglia, since these areas receive overactive EAA input from the subthalamic nucleus in Parkinsonism. Furthermore, injection of Compound I directly into the output regions of the basal ganglia alleviates Parkinsonian symptoms in both primate and rodent models of Parkinsonism.

For the therapeutic uses described above, the usual mammalian dosage range for a 70-kg human subject is from 0.01 to 10 mg per day or 0.001 mg to 1.0 mg per kg of weight per day; optionally in divided portions. Determinations of the proper dosage for a particular situation is within the skill of the art.

Pharmaceutical compositions of the compound of the present invention or its salts are produced by formulating the active compound in dosage unit form with a pharmaceutical carrier. Some examples of dosage unit forms are tablets, capsules, pills, powders, aqueous and nonaqueous oral solutions, and suspensions and parenteral solutions packaged in containers containing either one or some larger number of dosage units and capable of being subdivided into individual doses. Some examples of suitable pharmaceutical carriers, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol; glycerin; sorbitol; polyethylene glycol; water; agar; alginic acid; isotonic saline; and phosphate buffer solutions; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits, but for practical purposes it is preferably present in a concentration of at least 10% in a solid composition and at least 2% in a primarily liquid composition. The most satisfactory compositions are those in which a much higher proportion of the active ingredient is present.

Routes of administration of the subject compound or its salts are oral, parenteral, transdermal, or intranasal. For example, a useful intravenous dose is between 0.001 and 10 mg/kg. A preferred intravenous dose is 0.01 to 1 mg/kg. A still further preferred dose is 0.01 to 0.55 mg/kg. A useful oral dose is 0.01 to 30 mg/kg.

The following examples of formulations are provided to enable one skilled in the art to practice the invention. These examples are not intended to limit the scope of the invention in any way but rather to be illustrative thereof. Compound I is a compound of Formula I as described hereinbefore.

EXAMPLE 1

Injectables

Compound I, Water for injection USP q.s.

The hydrochloride salt of Compound I is dissolved in water and passed through a 0.2-micron filter. Aliquots of the filtered solution are added to ampoules or vials, sealed, and sterilized.

EXAMPLE 2

| Syrups 2 mg Compound I/5 ml syrup | |
|---|---|
| Compound I | 12.5 g |
| Purified Water USP | 200 ml |
| Cherry Syrup qu | 1000 ml |

EXAMPLE 3

| Capsules 0.5 mg, 1 mg, or 2 mg | |
|---|---|
| Compound I | 250 g |
| Lactose USP, Anhydrous q.s. or | 250 g |
| Sterotex Powder HM | 5 g |

Combine Compound I and the lactose in a tumble, blend for two minutes, blend for one minute with the intensifier bar, and then tumble blend again for one minute. A portion of the blend is then mixed with the Sterotex Powder, passed through a #30 screen and added back to the remainder of the blend. The mixed ingredients are then blended for one minute, blended with the intensifier bar for thirty seconds, and tumble-blended for an additional minute. The appropriately sized capsules are filled with 141 mg, 352.5 mg, or 705 mg of the blend, respectively, for the 50-mg, 125-mg, and 250-mg containing capsules.

EXAMPLE 4

| Tablets 0.5 mg, 1 mg, or 2 mg | |
|---|---|
| Compound I | 125 g |
| Corn Starch NF | 200 g |
| Cellulose, Microcrystalline | 46 g |
| Sterotex Powder HM | 4 g |
| Purified Water q.s. or | 300 ml |

Combine the corn starch, the cellulose, and Compound I together in a planetary mixer and mix for two minutes. Add the water to this combination and mix for one minute. The resulting mix is spread on trays and dried in a hot air oven at 50° C. until a moisture level of 1 to 2 percent is obtained. The dried mix is then milled with a Fitzmill through a #RH2B screen, and added back to the milled mixture and the total blended for five minutes by drum rolling. Compressed tablets of 0.150 mg, 3.75 mg, and 7.50 mg, respectively, of the total mix are formed with appropriate sized punches the 0.50 mg, 1.25 mg, or 5.00 mg containing tablets.

We claim:

1. A method for treating Parkinson's disease which comprises administering to a patient in need of said treatment a therapeutically effective amount of a compound in unit dosage form of formula or a pharmaceutically acceptable salt thereof wherein n is an integer of from one to six; either of X or Y is oxygen and the other is —CH$_2$—; R$_1$ is selected from a)

where R$_4$ and R$_5$ are independently hydrogen, fluorine, chlorine, bromine, nitro, trifluoromethyl, alkyl of from one to six carbon atoms, alkoxy of from one to six carbon atoms, or aryl;

b) 3,4,5-trimethylphenoxy;

c)

where R$_6$ is hydrogen, fluorine, chlorine, alkyl of from one to six carbon atoms, or aryl; Z is —CH$_2$—, —O—, —S—, or —NR$_7$— where R$_7$ is hydrogen, alkanoyl of from one to six carbon atoms, or alkyl of from one to six carbon atoms;

d)

wherein R$_8$ and R$_9$ are independently hydrogen, fluorine, bromine, alkyl of from one to six carbon atoms, or alkoxy of from one to four carbon atoms; or e)

where R$_8$ and R$_9$ are as defined above; where R$_2$ is methyl and R$_3$ is hydrogen, alkyl of from one to six carbon atoms, where R$_{10}$ is alkyl of from one to four carbon atoms; or where R$_2$ and R$_3$ when taken together with the nitrogen atom to which they are attached, form a piperidinyl or hexahydro-1H-azepinyl ring.

2. A method according to claim 1 wherein 0.001 mg to 10 mg/kg of weight per day of the compound or the pharmaceutically acceptable salt is administered.

3. A method for treating dystonia which comprises administering to a patient in need of said treatment a therapeutically effective amount of a compound in unit dosage form of formula or a pharmaceutically acceptable salt thereof, wherein n is an integer of from one to six; either of X or Y is oxygen and the other is —CH$_2$—; R$_1$ is selected from a)

where R$_4$ and R$_5$ are independently hydrogen, fluorine, chlorine, bromine, nitro, trifluoromethyl, alkyl of from one to six carbon atoms, alkoxy of from one to six carbon atoms, or aryl;

b) 3,4,5-trimethylphenoxy;

c)

where $R_6$ is hydrogen, fluorine, chlorine, alkyl of from one to six carbon atoms, or aryl; Z is —CH$_2$—, —O—, —S—, or —NR$_7$— where $R_7$ is hydrogen, alkanoyl of from one to six carbon atoms, or alkyl of from one to six carbon atoms;

d)

wherein $R_8$ and $R_9$ are independently hydrogen, fluorine, bromine, alkyl of from one to six carbon atoms, or alkoxy of from one to four carbon atoms; or e)

where $R_8$ and $R_9$ are as defined above; where $R_2$ is methyl and $R_3$ is hydrogen, alkyl of from one to six carbon atoms,

—CH$_2$—◁, —CH$_2$CH:CH$_2$, —CH$_2$C≡CH,

—CH$_2$CH$_2$—⌬, —CH$_2$CH$_2$—(thiophene),

—CH$_2$CH$_2$—(thiophene), or —CH$_2$CH$_2$—N(triazole-C(O)R$_{10}$)

where $R_{10}$ is alkyl of from one to four carbon atoms; or where $R_2$ and $R_3$ when taken together with the nitrogen atom to which they are attached, form a piperidinyl or hexahydro-1H-azepinyl ring.

4. A method according to claim 3 wherein 0.001 mg to 1 mg/kg of weight per day of the compound or the pharmaceutically acceptable salt is administered.

* * * * *